(12) United States Patent
Jennings et al.

(10) Patent No.: US 7,871,396 B2
(45) Date of Patent: Jan. 18, 2011

(54) BIFURCATION CATHETER ASSEMBLY AND METHOD

(75) Inventors: Adam Jennings, Buffalo, MN (US);
Daniel Quillin, Eden Prairie, MN (US);
Michael Meyer, Richfield, MN (US);
Kevin Grotheim, Maple Grove, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 450 days.

(21) Appl. No.: 11/554,396

(22) Filed: Oct. 30, 2006

(65) Prior Publication Data

US 2008/0171975 A1 Jul. 17, 2008

(51) Int. Cl.
*A61M 29/00* (2006.01)
(52) U.S. Cl. .................................... 604/101.01
(58) Field of Classification Search ........... 604/96.01, 604/101.01–101.05
See application file for complete search history.

(56) References Cited

U.S. PATENT DOCUMENTS

| | | | |
|---|---|---|---|
| 5,423,754 A * | 6/1995 | Cornelius et al. | 604/103 |
| 5,772,643 A * | 6/1998 | Howell et al. | 604/533 |
| 6,096,073 A | 8/2000 | Webster et al. | |
| 6,146,356 A | 11/2000 | Wang et al. | |
| 6,210,429 B1 | 4/2001 | Vardi et al. | |
| 6,325,826 B1 | 12/2001 | Vardi et al. | |
| 6,692,483 B2 | 2/2004 | Vardi et al. | |
| 6,706,062 B2 | 3/2004 | Vardi et al. | |
| 2003/0181923 A1 | 9/2003 | Vardi | |
| 2004/0138737 A1 | 7/2004 | Davidson et al. | |
| 2004/0176837 A1 | 9/2004 | Atladottir et al. | |
| 2005/0015108 A1 | 1/2005 | Williams et al. | |
| 2005/0102019 A1* | 5/2005 | Yadin | 623/1.11 |
| 2006/0155356 A1 | 7/2006 | Israel | |

FOREIGN PATENT DOCUMENTS

| | | |
|---|---|---|
| EP | 0 839 504 A1 | 5/1998 |
| WO | WO 96/02295 | 2/1996 |
| WO | 99/34749 | 7/1999 |
| WO | WO 00/27463 | 5/2000 |
| WO | WO 00/71055 A1 | 11/2000 |

OTHER PUBLICATIONS

U.S. Appl. No. 10/644,550, filed Aug. 21, 2003 entitled Stent With a Protruding Branch Portion for Bifurcated Vessels.
U.S. Appl. No. 60/776,149, filed Feb. 22, 2006 entitled Marker Arrangement for Bifurcation Catheter.

* cited by examiner

*Primary Examiner*—Nicholas D Lucchesi
*Assistant Examiner*—Nathan R Price
(74) *Attorney, Agent, or Firm*—Seager, Tufte & Wickhem, LLC

(57) ABSTRACT

A catheter assembly includes a main catheter branch and a side catheter branch. The main catheter branch includes first and second balloons. The side catheter branch is coupled to the second balloon. The side catheter branch can be coupled to the second balloon portion by passing through a pathway or receiver structure defined in the second balloon. The side catheter branch can also be coupled to the second balloon portion using a connector that connects the side catheter branch to a portion of the main catheter branch that carries the second balloon portion.

17 Claims, 13 Drawing Sheets

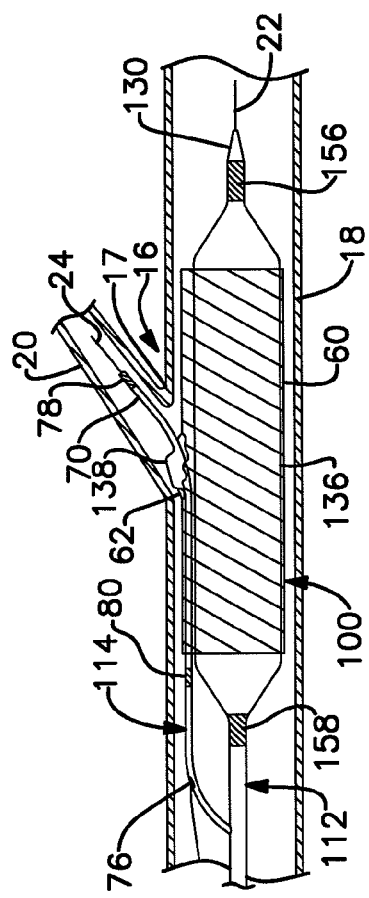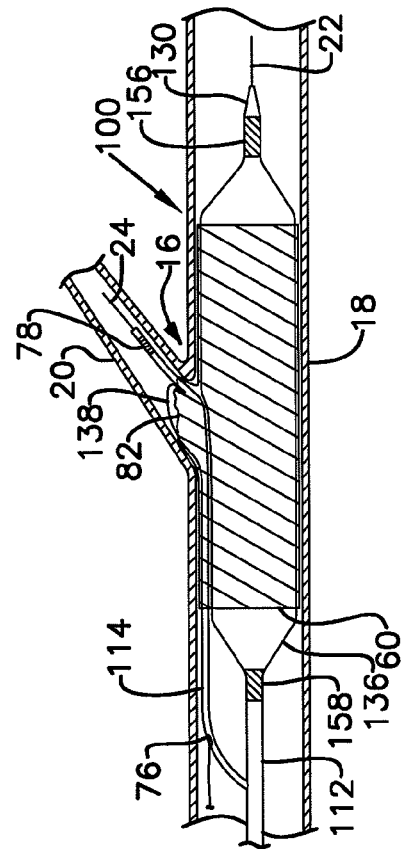

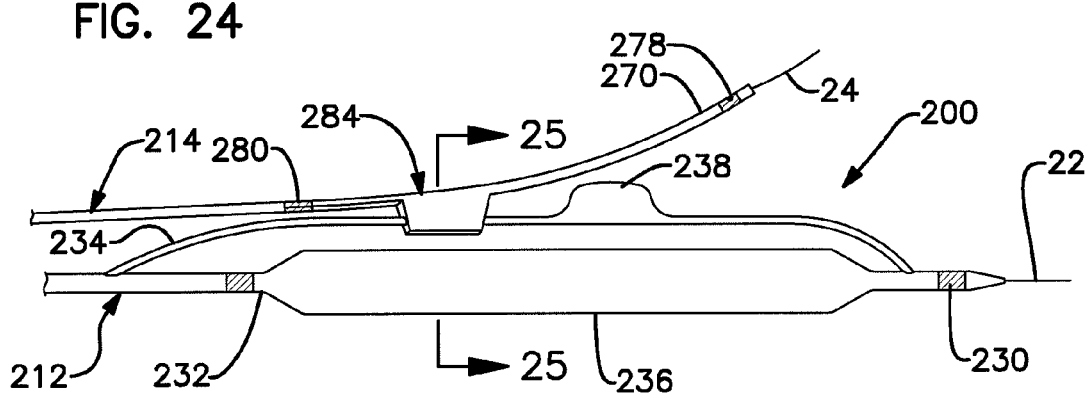
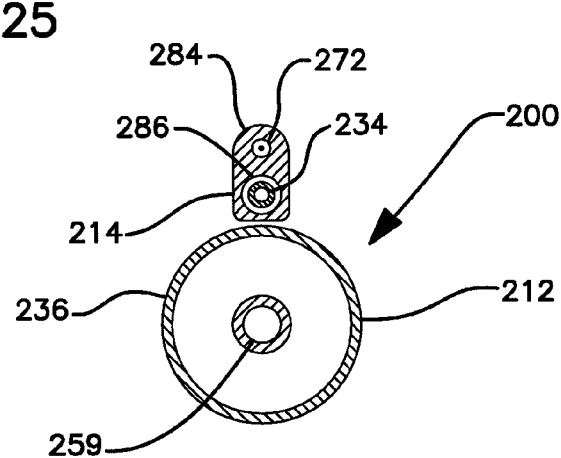
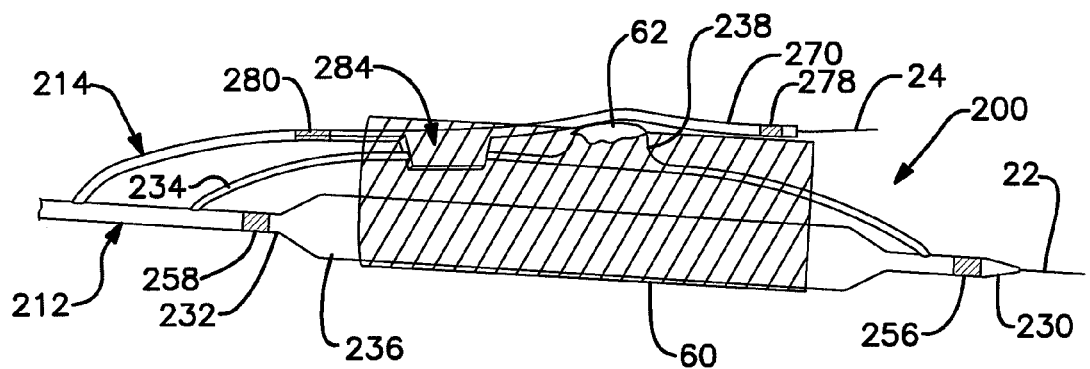

BIFURCATION CATHETER ASSEMBLY AND METHOD

TECHNICAL FIELD

This disclosure relates to bifurcation treatment systems and related methods of treating a bifurcated lumen. Preferred arrangements also relate to catheter configurations adapted for aligning features of the bifurcation treatment system relative to the bifurcated lumen.

BACKGROUND

Catheters are used with stents and balloon inflatable structures to treat conditions such as strictures, stenoses, and narrowing in various parts of the body. Various catheter designs have been developed for the dilatation of stenoses and to deliver and deploy stents at treatment sites within the body.

Stents are typically intraluminally placed by a catheter within a vein, artery, or other tubular shaped body organ for treating conditions such as, for example, occlusions, stenoses, aneurysms, dissection, or weakened, diseased, or abnormally dilated vessel or vessel wall, by expanding the vessel or by reinforcing the vessel wall. Stents can improve angioplasty results by preventing elastic recoil and remodeling of the vessel wall and treating dissections in blood vessel walls caused by balloon angioplasty of coronary arteries.

While conventional stent technology is relatively well developed, stent technologies related to treatment of the region of a vessel bifurcation are still being developed.

SUMMARY OF THE DISCLOSURE

The illustrated examples disclosed herein relate generally to catheter assemblies and related methods for treatment of a vessel bifurcation. The catheter assembly includes features that improve alignment of the catheter assembly with an ostium of a branch vessel of the vessel bifurcation. An example catheter assembly includes a main catheter branch configured to reside within the main vessel, and a side catheter branch configured to extend from the main vessel into the branch vessel.

In one example, the main catheter branch includes first and second balloon portions. The side catheter branch is coupled to the second balloon portion. Coupling the side catheter branch and the second balloon portion can facilitates relative radial alignment of the side catheter branch with the second balloon portion. The coupling can result from the side catheter branch extending through a pre-formed side catheter branch recess that is defined in the second balloon portion. Alternatively, the coupling can result from a connector used to secure the side catheter branch to the second balloon portion.

There is no requirement that an arrangement include all features characterized herein to obtain some advantage according to this disclosure.

BRIEF DESCRIPTION OF THE DRAWINGS

FIG. 22 is a schematic side view showing the catheter assembly of FIG. 19 with the side branch catheter positioned in a branch vessel.

FIG. 23 is a schematic side view showing the catheter assembly of FIG. 19 with the first and second balloons inflated.

FIG. 24 is a side perspective view of another example catheter assembly, wherein the side catheter branch includes a truncated dual lumen connector through which a portion of the main catheter branch extends.

FIG. 25 is a cross-sectional view of the catheter assembly shown in FIG. 24 taken along indicators 25-25.

FIG. 26 is a side perspective view of the catheter assembly of FIG. 24 arranged with a stent.

DETAILED DESCRIPTION

I. General Background

Figure 1A:
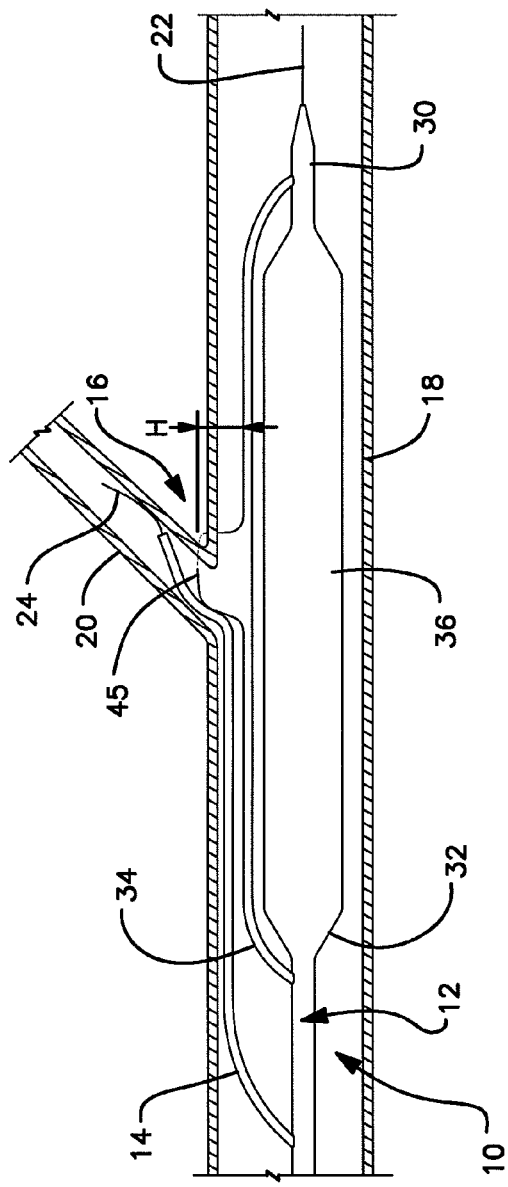
FIG. 1A is a schematic side view of an example prior art catheter assembly positioned within a vessel bifurcation.

This disclosure relates to bifurcation treatment systems and related methods of treating bifurcations in a patient's body. The term bifurcation means a division location from one unit into two or more units. Generally, two types of bifurcations of a body organ include 1) a main tubular member defining a main lumen and a branch tubular member defining a branch lumen that extends or branches off from the main tubular member, wherein the main and branch lumens are in fluid communication with each other, and 2) a primary or main member defining a primary or main lumen (also referred to as a parent lumen) that splits into first and second branch members defining first and second branch lumens. The term lumen means the cavity or bore of a tubular structure such as a tubular organ (e.g., a blood vessel). The term conduit means a channel (e.g., a pipe or tube) through which something such as a fluid is conveyed. The terms lumen and conduit are used interchangeable throughout this document.

An example bifurcation is a vessel bifurcation that includes a continuous main vessel and a branch vessel, wherein the vessels define a main lumen and a branch lumen, respectively that are in fluid communication with each other. A vessel bifurcation can alternatively include a parent vessel that divides into first and second branch vessels, wherein the vessels define a parent lumen and first and second branch lumens, respectively, which lumens are all in fluid communication with each other.

The disclosed systems and methods include a catheter shaft, a main catheter branch, a side catheter branch, and an inflatable member which when inflated extends in a direction radially outward from the main catheter branch. The term side catheter branch is defined as a portion of a catheter assembly that is configured to extend from a main vessel into a branch vessel of a vessel bifurcation. Typically, the side catheter branch defines a guidewire lumen sized for passing the side catheter branch over a branch guidewire, wherein the branch guidewire is suitable for passing into the branch vessel. Each of the catheter shaft, main catheter branch, and side catheter branch can define multiple lumens or conduits, wherein each lumen or conduit has a specific structure and function (e.g., sized to receive a guidewire or configured to pass inflation fluid). When multiple lumen are present in a single catheter branch, the lumens can extend co-lineally (e.g., side-by-side) or coaxially (one within the other).

The term main catheter branch is defined as a portion of a catheter assembly that remains in a first or main vessel of the vessel bifurcation when the side catheter branch is extending into a second or branch vessel of the vessel bifurcation. The at least one inflatable member is typically positioned on the main catheter branch. Additional inflatable members can be positioned on the side catheter branch.

In one example, the main catheter branch can include first and second balloon portions. The first balloon portion is an elongate balloon positioned on a main lumen of the main catheter branch. The second balloon portion is the inflatable member and is positioned on a branch lumen of the main catheter branch.

In another example, the main catheter branch defines only a single branch. The main lumen includes first and second balloon portions, wherein the first balloon portion is an elongate balloon and the second balloon portion is the inflatable member. The second balloon portion is integral with the first balloon portion.

In some of the examples described herein, the inflatable member, when positioned on the main catheter branch, is couples the side catheter branch to the main catheter branch. For example, the side catheter branch can be directly connected to the inflatable member. In an arrangement in which the main catheter branch includes main and branch lumens, the side catheter branch can be connected to the branch lumen.

An attachment member can be used to connect the side catheter branch to the main catheter branch. An example attachment member includes a dual lumen connector that defines one lumen through which the side catheter branch passes and a second lumen through which a portion of the main catheter branch passes. In one arrangement, the first lumen of the dual lumen connector is sized to receive the side branch guidewire lumen, and the second lumen of the dual lumen connector is sized to receive an inflation lumen that is used to inflate the inflatable member.

The inflatable member can include a single inflatable portion having structure configured for connection of the side catheter branch. A single inflatable portion can have a variety of shapes and sizes that provide the desired opening or receiver structure through which the side catheter branch can extend. An example single inflatable portion is bent into a desired shape and bonded to itself to define the opening or receiver structure through which the side catheter branch passes.

Alternatively, the inflatable member can include two or more inflatable portions positioned adjacent to each other that define an opening or receiver structure through which the side catheter branch passes. For example, a configuration with multiple inflatable portions can define an opening at an interface between the multiple portions through which the side catheter branch can extend. In some arrangements, at least some of the multiple portions can be secured to each other. The example systems and methods described below with reference to the attached FIGS. 3A-18 illustrate some example multiple inflatable member configurations.

A variety of stents can be used with the systems and methods disclosed herein. Examples of such stents can be found in, for example, in U.S. Pat. Nos. 6,210,429, 6,325,826 and 6,706,062 to Vardi et al., co-pending U.S. patent application Ser. No. 10/644,550, filed on Aug. 21, 2003, and titled STENT WITH A PROTRUDING BRANCH PORTION FOR BIFURCATED VESSELS, and U.S. Published Patent Application No. 2004/0176837 titled SELF-EXPANDING STENT AND CATHETER ASSEMBLY AND METHOD FOR TREATING BIFURCATIONS, the entire contents of which are incorporated herein by reference. In general, the aforementioned stents include a lateral branch opening located on a sidewall of the stent at a location between distal and proximal open ends of the stent. The lateral branch opening defines a path between an inner lumen of the stent and an area outside of the stent. The stent lateral branch opening is distinct from the cell openings defined between strut structures from which the stent sidewall is constructed. In some stents, the lateral branch opening can be surrounded by expandable structure. The expandable structure can be configured to extend radially into the branch lumen of the bifurcation upon expansion of, for example, an inflatable portion of the bifurcation treatment system. Typically, the stent is expanded after being positioned in the main vessel of the vessel bifurcation with the lateral branch opening aligned with an opening into the branch vessel. Alignment of the lateral branch opening with the opening into the branch vessel includes requires radial and axial alignment. The stent, including the expandable structure surrounding the lateral branch opening, can be expanded with a single expansion or multiple expansions using one or more inflatable balloons.

II. Example Shown in FIGS. 1A-2B

An illustrated view of an example bifurcation treatment catheter 10 is shown in FIGS. 1A-2B. System 10 includes a main catheter branch 12 and a side catheter branch 14. The main catheter branch 12 includes a distal end 30, first and second branch portions 32, 34, and first and second inflatable members 36, 38 (also referred to herein as main and branch balloons) associated with the branch portions 32, 34, respectively. The inflatable member 36 is typically an elongate tube-shaped structure sized to traverse the vessel bifurcation 16 (i.e., extend from proximal of to distal of an ostium of branch vessel 20). The second inflatable member 38 is typically shorter in length than the first inflatable member 36 and sized to at least partially extend into the branch vessel 20. The second inflatable member 38 typically primarily extends in a direction radially outward from the main catheter branch 12.

The main catheter branch 12 includes a guidewire lumen 31 that extends through the inflatable member 36, and an inflation lumen 33 that is in fluid communication with the inflatable member 36 for filling and draining the inflatable member 36. The second branch portion defines an inflation lumen for filling and draining the second inflatable member 38. The main catheter branch 12 is configured to remain in the main vessel 18. The main catheter branch 12 typically has a larger cross sectional profile as compared to the side catheter branch 14.

The side catheter branch 14 typically includes a guidewire lumen 15. In some examples (e.g., see FIGS. 19-23 described below), the side catheter branch 14 includes an inflatable member that is separate and distinct from the inflatable members 36, 38, and a separate inflation lumen in fluid communication with the inflatable member on the side catheter branch 14.

The first inflatable member 36 is an elongate balloon structure that extends along a length of the first branch portion 32. The second inflatable member, when inflated, extends in a radial direction relative to the first branch portion 32. The second inflatable member 38 includes distal and proximal sides 40, 42 (e.g., see FIGS. 3B-8). When inflated, the second inflatable member 36 has a height H (see FIG. 7) measured in the radial direction. The height H is measured between a surface 45 of the inflatable member 36 facing radially away from the elongate second branch portion 34 and an outer surface of the second branch portion 34. The inflated second inflatable member 38 can at least partially extend from a main vessel 18 into a branch vessel 20 of the vessel bifurcation 16 for treatment of the vessel bifurcation 16 (e.g., see FIG. 3B).

The inflatable members 36, 38 can be configured as inflatable balloon structures. Balloon structures are defined as inflatable members constructed of a material that retains a fluid, without restriction to the type of fluid retained (e.g., liquid or gas) or the type of material used (e.g., compliant, non-compliant, semi-compliant material) for the balloon. Balloon structures are typically both expandable and retractable.

The inflatable members 36, 38 can be constructed of any suitable material. The inflatable members 36, 38 can be configured as inflatable balloons structures. The inflatable members 36, 38 and all other balloons disclosed herein can be made of any suitable balloon material including compliant and non-compliant materials and combinations thereof. Some example materials include thermoplastic polymers, polyethylene (high density, low density, intermediate density, linear low density), various co-polymers and blends of polyethylene, ionomers, polyesters, polycarbonates, polyamides, poly-vinyl chloride, acrylonitrile-butadiene-styrene copolymers, polyether-polyester copolymers, and polyetherpolyamide copolymers. One suitable material is Surlyn®, a copolymer polyolefin material (DuPont de Nemours, Wilmington, Del.). Still further suitable materials include thermoplastic polymers and thermoset polymeric materials, poly (ethylene terephthalate) (commonly referred to as PET), thermoplastic polyamide, polyphenylene sulfides, polypropylene. Some other example materials include polyurethanes and block copolymers, such as polyamide-polyether block copolymers or amide-tetramethylene glycol copolymers. Additional examples include the PEBAX® (a polyamide/polyether/polyester block copolymer) family of polymers, e.g., PEBAX® 2533, 5533, 6333, 7033, or 7233 (available from Arkema, Philadelphia, Pa.). Other examples include nylons, such as aliphatic nylons, for example, Vestamid L21011F, Nylon 11 (Arkema), Nylon 6 (Honeywell), Nylon 6/10 (BASF), Nylon 6/12 (Ashley Polymers), or Nylon 12. Additional examples of nylons include aromatic nylons, such as Grivory (EMS) and Nylon MXD-6. Other nylons and/or combinations of nylons can also be used. Still further examples include polybutylene terephthalate (PBT), such as CELANEX® (available from Ticona, Summit, N.J.), polyester/ether block copolymers such as ARNITEL® (available from DSM, Erionspilla, Ind.), e.g., ARNITEL® EM740, aromatic amides such as Trogamid (PA6-3-T, Degussa), and thermoplastic elastomers such as HYTREL® (Dupont de Nemours, Wilmington, Del.). In some embodiments, the PEBAX®, HYTREL®, and ARNITEL® materials have a Shore D hardness of about 45D to about 82D. The balloon materials can be used pure or as blends. For example, a blend may include a PBT and one or more PBT thermoplastic elastomers, such as RITEFLEX® (available from Ticona), ARNITEL®, or HYTREL®, or polyethylene terephthalate (PET) and a thermoplastic elastomer, such as a PBT thermoplastic elastomer. Additional examples of balloon material can be found in U.S. Pat. No. 6,146,356, which is incorporated herein by reference.

Typically, the second inflatable portion 38 is longitudinally positioned at a midpoint of the first inflatable portion 36 measured from distal and proximal ends of the first inflatable portion 36. Alternative applications can include a second inflatable portion 38 that is positioned at any longitudinal location along a length of the first inflatable portion 36.

In the example shown in FIGS. 1A-2B, the first and second branch portions 32, 34 have a common inflation lumen 33. The term inflation lumen means a cavity of a tubular structure through which fluid passes for inflation and deflation of an inflatable member. Alternatively, the branch portions 32, 34 have separate inflation lumens. The inflation lumen can extend from the branch portions 32, 34 to a proximal portion of the system 10 that remains outside of the patient. The inflation lumen can portion of the system 10 that remains outside of the patient. The inflation lumen can simultaneously be in fluid communication with the interiors of the first and second inflatable portions 36, 38. The inflation lumen is used to supply pressurized inflation fluid to the inflatable members 36, 38 and to drain inflation fluid from the inflatable members 36, 38 when it is desired to deflate the members 36, 38. The first and second inflatable members 36, 38 are initially at least partially deflated when advancing the system 10 through the patient into the bifurcation 16. In the examples shown in FIGS. 1A-2B, the inflation lumen inflates the inflatable members 36, 38 substantially simultaneously.

In an alternative example, the inflatable members 36, 38 are in fluid communication with separated inflation lumens. The use of separate inflation lumens can provide for simultaneous or sequential inflation of the members 36, 38. A typical sequential inflation process includes inflating the first inflatable member 36 followed by inflation of the second inflatable member 38, followed by deflation of the inflatable members 36, 38 in any desired order.

The main and side catheter branches 12, 14 each define a guidewire lumen (not shown) sized to receive a guidewire. In operation, a main guidewire 22 is positioned within the main vessel 18 with a distal end of the guidewire 22 oriented at a position distally beyond the bifurcation 16. A branch guidewire 24 is positioned within a branch vessel 20 with a distal end of the guidewire 24 oriented distally beyond the bifurcation 16. A proximal end of the guidewire 22 is fed into the guidewire lumen at the distal end of the main catheter branch 12. A proximal end of the branch guidewire 24 is fed into the guidewire lumen of the side catheter branch 14 at a distal end of the side catheter branch. The main and side catheter branches 12, 14 are then advanced over the guidewires 22, 24 to the vessel bifurcation 16. The main catheter branch 12 is advanced distally to a position where the second inflatable member 38 is positioned generally in alignment with an ostium into the branch vessel 20. The side catheter branch 14 is advanced over guidewire 24 until a distal end of the side catheter branch 14 is positioned within branch vessel 20.

The example bifurcation catheters and systems disclosed herein can be used in over-the-wire or rapid exchange systems. Rapid exchange is described in one exemplary embodiment in U.S. Published Appl. No. 2003/0181923 to Vardi et al., which is incorporated herein by reference.

Figure 2A:
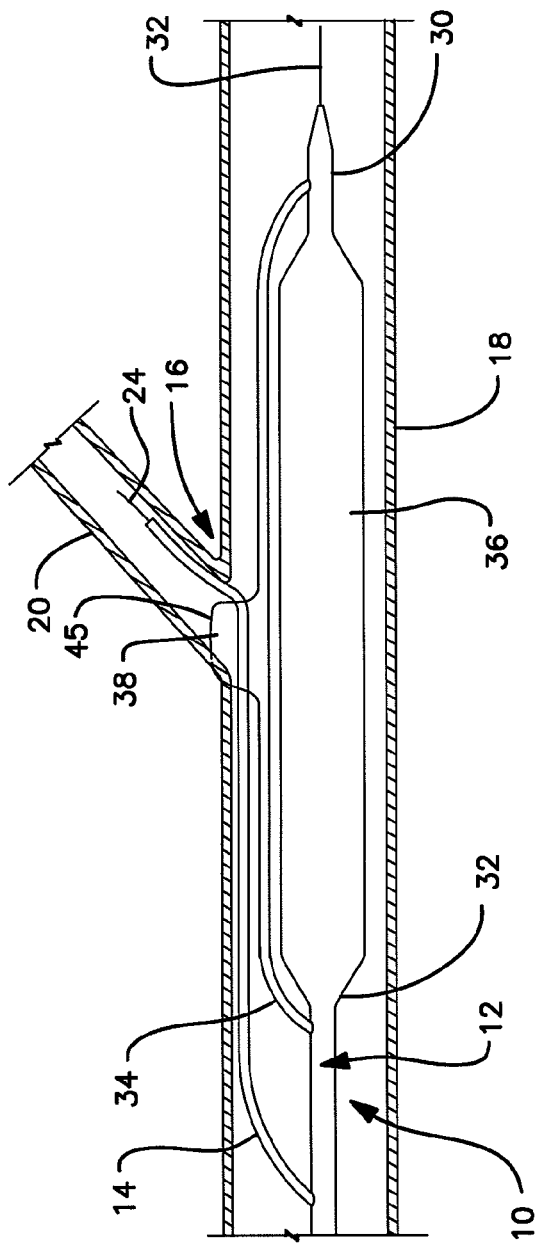
FIG. 2A is a schematic side view of another example prior art catheter assembly positioned within a vessel bifurcation.

Typically, a more effective treatment of the vessel bifurcation 16 occurs when the second inflatable member 38 is aligned both axially and radially relative to the ostium into branch vessel 20 prior to inflation of the first and second inflatable members 36, 38. FIGS. 1A and 2A illustrate misaligned axial positioning of the second inflatable member 38 relative to the ostium into branch vessel 20. In FIG. 1A, the second inflatable member 38 is misaligned in a distal direction, which results in undesired overlap of the carina 17 of the vessel bifurcation and a gap between a proximal side 42 of the inflatable member 38 and a proximal side of the ostium into branch vessel 20. In FIG. 2A, the second inflatable member 38 is misaligned in a proximal direction, which results in an undesired gap between the distal side 40 of the second inflatable member 38 and the carina 17 of the vessel bifurcation. Radial misalignment can result in gaps between at least one of the lateral sides of the second inflatable member 38 and lateral sides of the ostium into the branch vessel 20. Radial and axial misalignment can cause overlap of the second inflatable member with portions of the vessel wall that results in undesired stress or damage on the vessel wall. Misalignment in the axial, radial or both axial and radial directions of the second inflatable member 38 relative to the ostium into branch vessel 20 can result in overall less effective treatment of the vessel bifurcation 16.

Figure 1B:
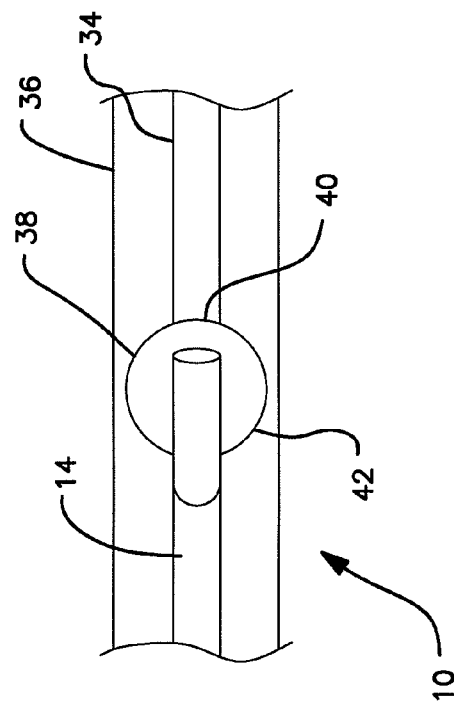
FIG. 1B is a schematic top view of the catheter assembly shown in FIG. 1.
Figure 2B:
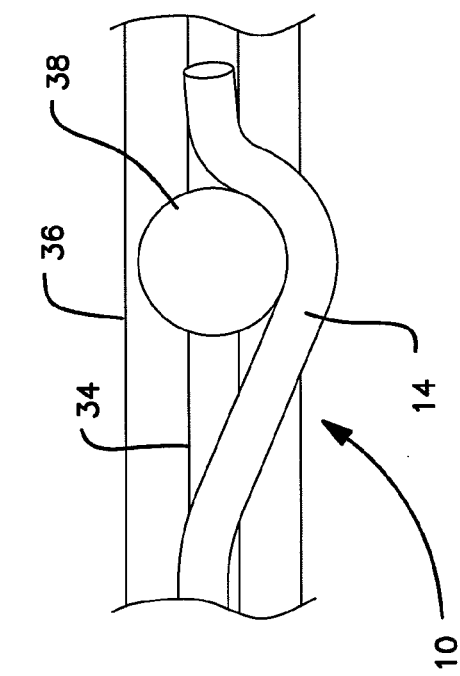
FIG. 2B is a schematic top view of the catheter assembly shown in FIG. 3.

Using the side catheter branch 14 to axially and radially align the second inflatable member 38 relative to the ostium of branch vessel 20 before and during inflation of the inflatable members 36, 38 can involve some challenges. One challenge involves maintaining a fixed orientation of the side catheter branch 14 relative to the second inflatable member 38. FIGS. 1A-B illustrate the side catheter branch 14 positioned along a proximal side 42 of the at least partially inflated second inflatable member 38. The curved surfaces of the second inflatable member 38 tend to permit the second inflatable member 38 to rotate and be displaced axially relative to the side catheter branch 14. FIGS. 2A-B illustrate the second inflatable member 38 displaced proximally and rotated such that the side catheter branch 14 is now positioned along a lateral side 41 and distal side 40 of the second inflatable member 38. Because there is no connection between side catheter branch 14 and the second inflatable member 38 in FIGS. 1A-2B, the second inflatable member 38 can move into a misaligned positioned relative to the ostium of the branch vessel 20. The second inflatable member 38 can move into misaligned positions (e.g., the distal side 40 positioned distally of the carina 17 of vessel bifurcation 16 in FIG. 1A) without the side catheter branch 14 moving relative to the branch vessel 20. In some instances, both the side catheter branch 14 and second inflatable member 38 move relative to each other and relative to the ostium of branch vessel 20 resulting in at least one of radial and axial misalignment of the second inflatable member 38 relative to the ostium of branch vessel 20.

Even if the relative position between the side catheter branch 14 and second inflatable member 38 remains constant and predictable, misalignment of the second inflatable member 38 relative to the ostium of branch vessel 20 can still exist. As shown in FIGS. 1A and 2A, the size of the side catheter branch 14 when positioned adjacent to the at least partially inflated second inflatable member 38 within the ostium tends to shift the second inflatable member 38 into misalignment axially. Similar radial misalignment can occur depending on the relative position of the side catheter branch 14 to the second inflatable member 38 within the ostium of the branch vessel 20.

A configuration of the second inflatable member 38 that helps to center the side catheter branch 14 relative to a center portion of the second inflatable member 38 can help to axially and radially align the second inflatable member 38 relative to the branch vessel 20. Further, connection of the side catheter branch 14 to the second inflatable member 20 can reduce movement of the second inflatable member 38 and side catheter branch 14 relative to the branch vessel prior to and during inflation of the inflatable members 36, 38.

III. The Side Branch Balloon Examples Shown in FIGS. 3-18

Figure 3A:
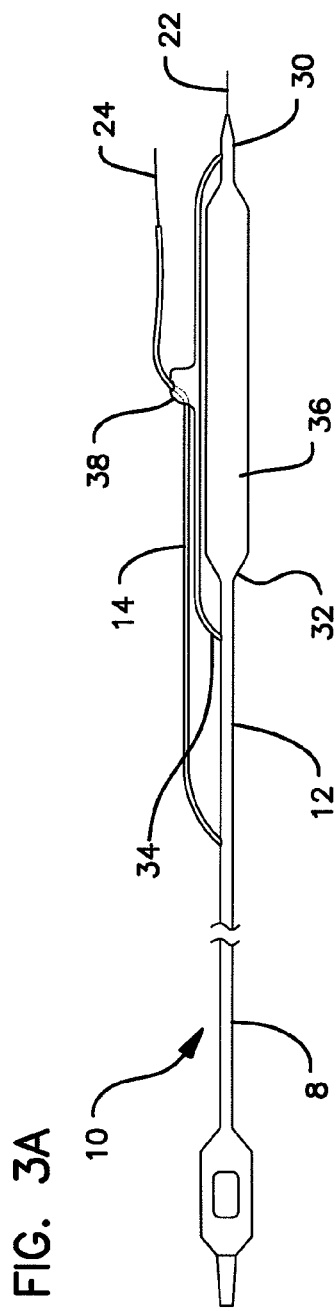
FIG. 3A is a schematic side view of an example catheter assembly in accordance with inventive principles disclosed herein, a balloon of the catheter assembly defining an aperture through which the side catheter branch can extend.
Figure 3B:
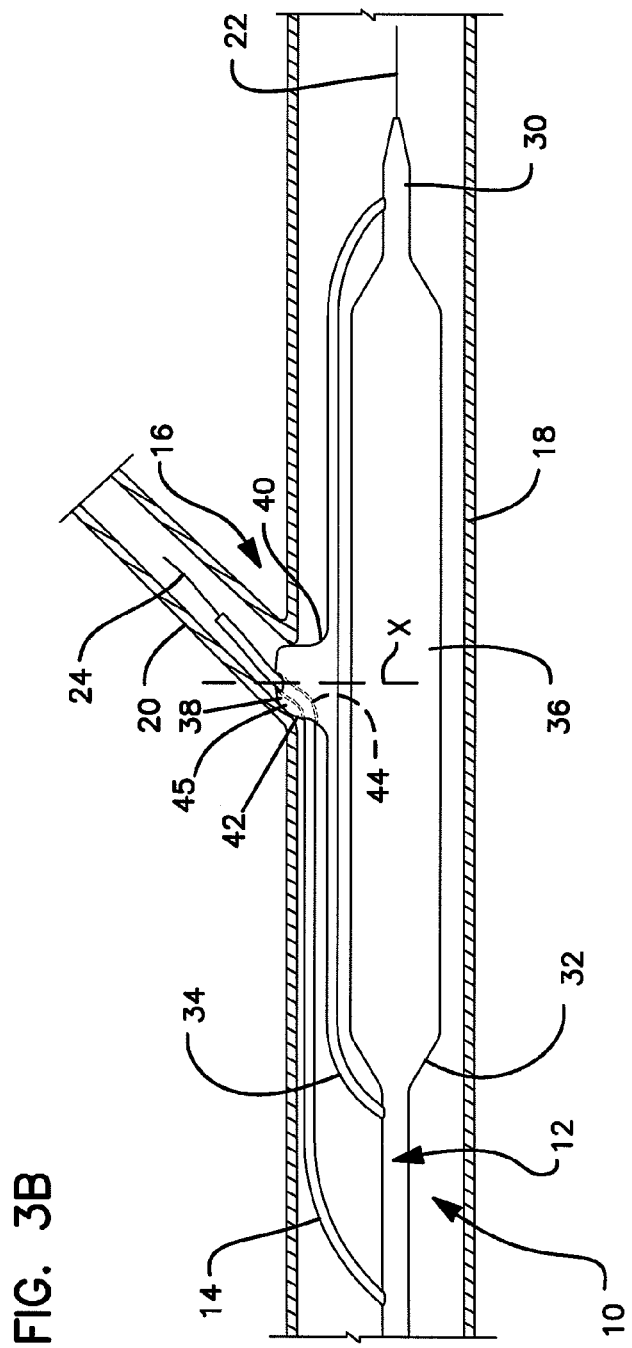
FIG. 3B is a schematic side view of a distal end arrangement of the catheter assembly shown in FIG. 3A.

Referring now to FIGS. 3A and 3B, a bifurcation treatment catheter 100 is shown and described. The catheter 100 includes an elongate proximal trunk 8 that extends from outside the patient to the distal end features (e.g., proximal of an intersection between a proximal end of the main catheter branch portion 34 and the branch portion 32) of the catheter 10. The second inflatable member 38 of the catheter 100 at least partially defines a passage 44 through which the side catheter branch 14 extends. The passage 44 can also be referred to as a side catheter branch receiver. The passage 44 is structured for the side catheter branch to extend through or be received in the passage 44. The passage 44 is pre-formed in the second inflatable member 38. The passage 44 exists before and after inflation of the second inflatable member 38. Further, the passage 44 is defined in the second inflatable member 38 when the side catheter branch 14 is not extending through the passage 44. The size and shape of the passage 44 can change during inflation and deflation of the second inflatable member, but maintains structure sufficient for the side catheter branch to pass through in any inflated or deflated state. The passage 44 can have any desired shape and size. The passage 44 can be defined by any number of parts or portions of the second inflatable member 38 or other portions of the main catheter branch 12. The examples shown in FIGS. 3-18 illustrate various sizes, shapes and configurations for the passage 44. For example, the passage 44 can be shaped as a conduit, a channel, or groove of any desired cross-sectional shape.

The passage 44 provides a connection between the side catheter branch 14 and the main catheter branch 12 via the second inflatable member 38. The connection between the side catheter branch 14 and second inflatable member 38 minimizes relative movement between side catheter branch 14 and the second inflatable member 38. Further, when the side catheter branch 14 extends through the second inflatable member 38 and out of a surface 45 that faces into the branch vessel 20, the side catheter branch does not occupy space around an inner circumference of the ostium of branch vessel 20 during inflation of the second inflatable member 38 that would otherwise tend to partially misalign the second inflatable member 38 relative to the branch vessel (e.g., see the axial misalignment shown in FIGS. 1A and 2A).

The passage 44 has an outlet at a generally centered location on the outward facing surface 45 of the second inflatable member 38 that faces into the branch vessel 20. FIG. 3B illustrates a central axis X passing through a centered location on the outward facing surface 45. The passage 44 includes an inlet along the proximal side 42. The inlet can be positioned on the second inflatable member 38 as shown in FIGS. 3A-B. Alternatively, the inlet can be defined between the second inflatable member 38 and the catheter member to which the second inflatable member 38 is secured (e.g., the space defined between the second inflatable member 38 and the branch portion 34 shown in FIG. 15). Extending the second inflatable member 38 through the passage 44 can reduce radial rotation and axial movement of the second inflatable member 38 relative to the ostium in the branch vessel 20 as the inflatable member 38 is inflated.

Figure 4:
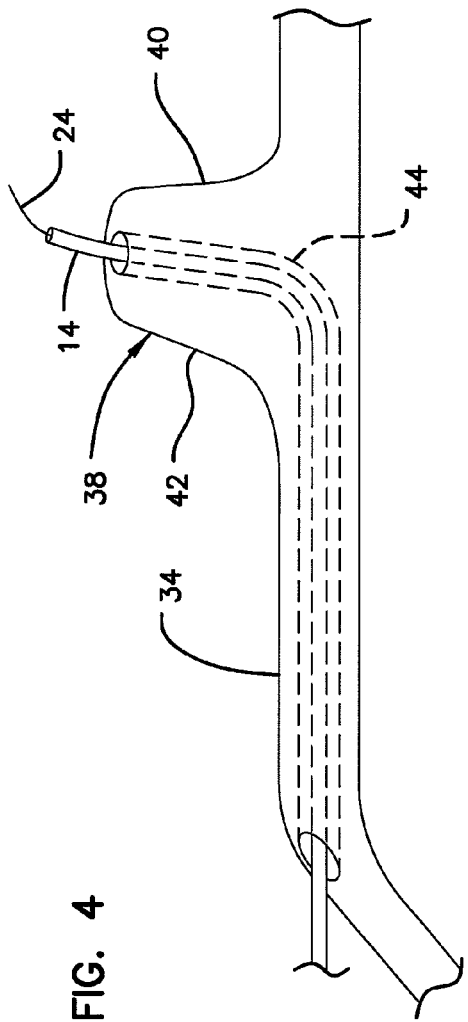
FIG. 4 is a schematic side view of an example catheter assembly having a conduit defined in a balloon and a branch member of the catheter assembly, the conduit sized to receive a side catheter branch.

Referring now to FIG. 4, an alternative arrangement for the passage 44 is shown. The passage 44 shown in FIG. 4 extends from the surface 45 through an interior of the second inflatable member 38, and through at least a portion of the catheter member (e.g., the branch portion 34) on which the second inflation member 38 is positioned. The passage 44 can exit the catheter member (e.g., branch portion 34) at any point along the length of the second branch portion 34 typically proximally of the second inflatable member 38. Alternatively, the passage 44 remains within the catheter member (e.g., branch portions 34 and 32) to a point outside of the patient.

Figure 5:
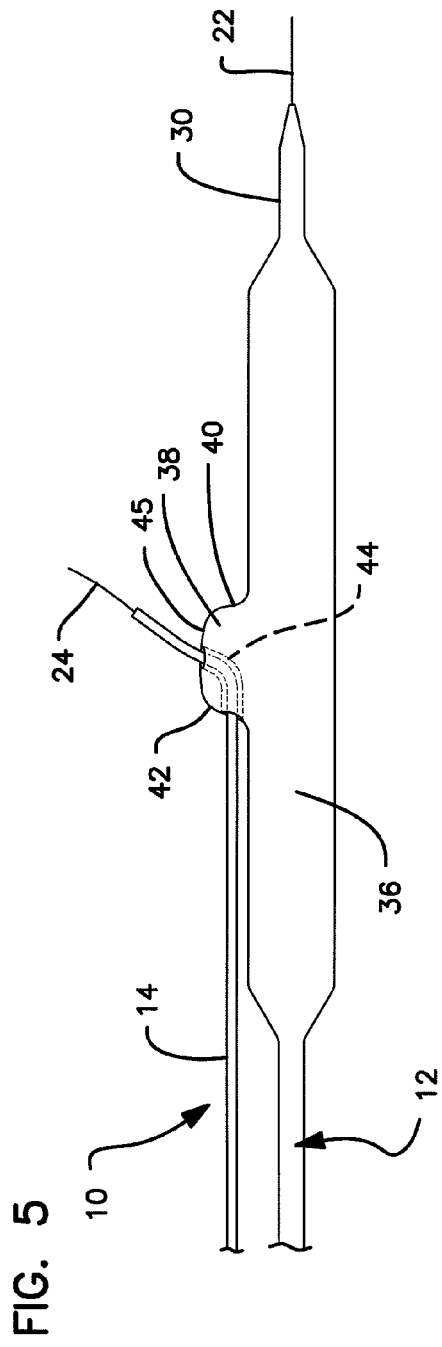
FIG. 5 is a schematic side view of another example catheter assembly having a main catheter branch that includes first and second balloons secured to each other, wherein the second balloon defines an opening through which the side catheter branch can extend.

Referring now to FIG. 5, a bifurcation treatment catheter 100 is shown including the second inflatable member 38 positioned on the first inflatable member 36. The second inflatable member 38 can be integrally formed as a single piece with the first inflatable member 36. Alternatively, the second inflatable member 38 can be a separate piece that is connected or otherwise mounted to the first inflatable member 36. A passage 44 defined in the second inflatable member 38 can have similar features and functions as described with reference to FIG. 3B above. Extending the side catheter branch 14 through the passage 44 when the second inflatable member 38 is positioned on the first inflatable member 36 can further reduce radial movement of the second inflatable member 38 as compared to the configuration shown in FIG. 3B. The second branch 34 shown in FIG. 3B can rotate slightly relative to the first branch 32. The extent of the rotation between branches 32, 34 depends in part on, for example, the length of the branches 32, 34, the connection point of proximal and distal ends of the branch 34 to the branch 32, and the materials used for the branches 32, 34.

Figure 6:
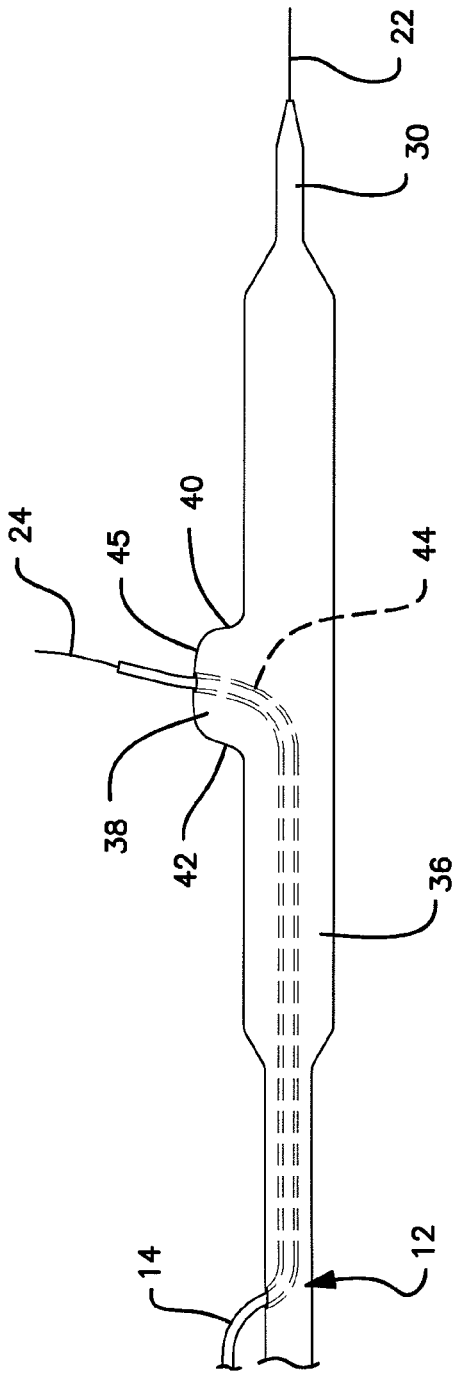
FIG. 6 is a schematic side view of another example catheter assembly having a main catheter branch that includes first and second balloons to each other, wherein the second balloon member and branch portion of the main catheter branch define a conduit through which the side catheter branch can extend extends.

Referring now to FIG. 6, an alternative arrangement for the passage 44 is shown. The passage 44 shown in FIG. 4 extends from the outward facing surface 45 through at least a portion of an interior of the main catheter branch 12. The passage 44 can exit the second branch portion 34 at any point along the length of the main catheter branch at a location typically proximal of the second inflatable member 38. Alternatively, the passage 44 extends within the main catheter branch 12 to a point outside of the patient.

Figure 8:
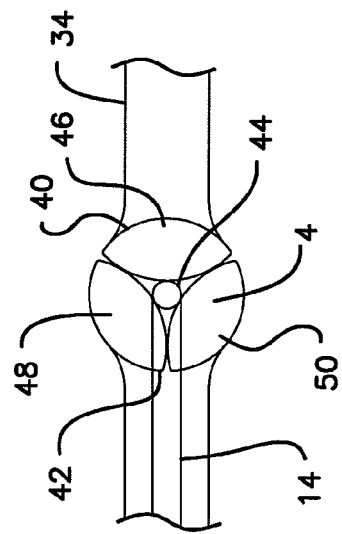
FIG. 8 is a top view of the balloon arrangement shown in FIG. 7.
Figure 7:
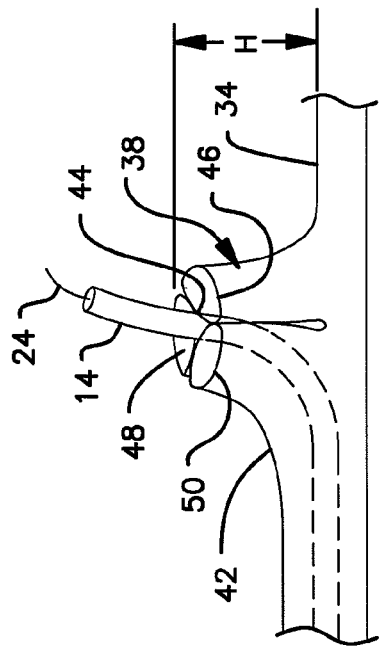
FIG. 7 is a schematic side view of an example balloon arrangement that includes three balloon members defining a center distal opening and a side proximal opening between balloon members.

FIGS. 7 and 8 illustrate the use of multiple portions or segments in the second inflatable member 38 which when inflated define the passage 44 through which the side catheter branch 14 extends. The arrangement shown in FIGS. 7 and 8 includes first, second and third portions 46, 48, 50 of the second inflatable member 38. The side catheter branch 14 extends into the passage 44 between the first and second portions 46, 48, and extends out of the passage 44 at the front face 45 between the first, second and third portions 46, 48, 50. The opening of passage 44 on the front face is generally centered in the second inflatable member 38. The portions 46, 48, 50 can be connected together at some point along the height H. For example, the interface between second and third portions 48, 50 at the top face can be connected together with a heat weld or with adhesives. This connection between portions 48, 50 would inhibit movement of the side catheter branch 14 from the second inflatable member 38 through the interface between the portions 48, 50.

Figure 11:
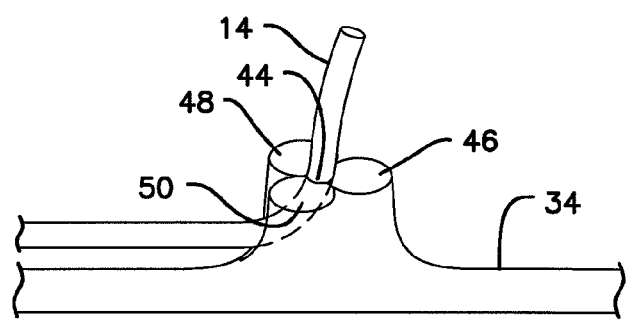
FIG. 11 is a schematic side view of an example balloon arrangement comprising three cylindrical shaped inflatable portions defining a center distal opening and a side proximal opening
Figure 12:
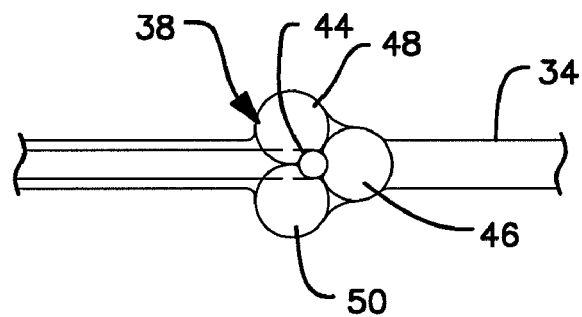
FIG. 12 is a top view of the balloon arrangement of FIG. 11.
Figure 13:
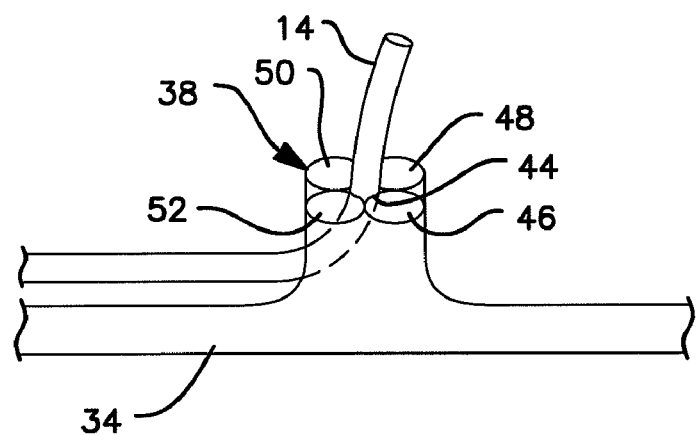
FIG. 13 is a schematic side view of an example balloon arrangement comprising four cylindrical shaped inflatable members defining a center distal opening and a side proximal opening
Figure 14:
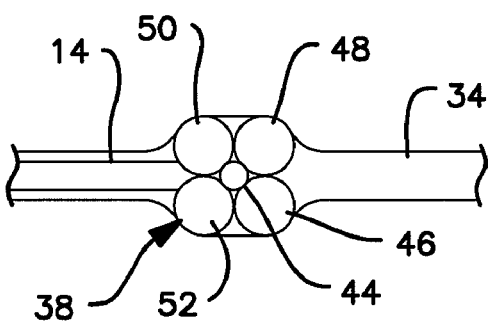
FIG. 14 is a top view of the balloon arrangement of FIG. 13.

The portions 46, 48, 50 have a generally oblong or oval shape as viewed from the top surface (see FIG. 8) in this example. Other shapes for the portions 46, 48, 50 of the second inflatable member 38 can be used to provide the same or similar function. For example, FIGS. 11 and 12 illustrate three generally cylindrical portions 46, 48, 50 having a circular cross section that defines the passage 44. In another example shown in FIGS. 13 and 14, four portions 46, 48, 50, 52 are used to define the passage 44.

Figure 9:
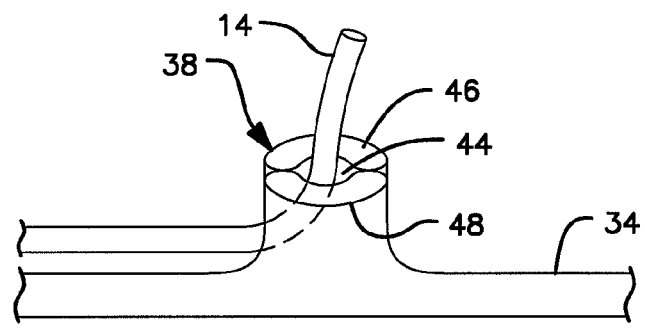
FIG. 9 is a schematic side view of an example balloon arrangement having two balloon members defining a center distal opening and a side proximal opening.
Figure 10:
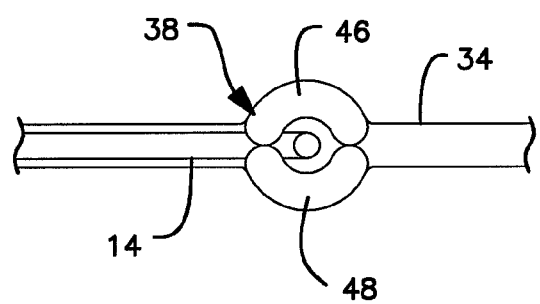
FIG. 10 is a top view of the balloon arrangement of FIG. 9.
Figure 17:
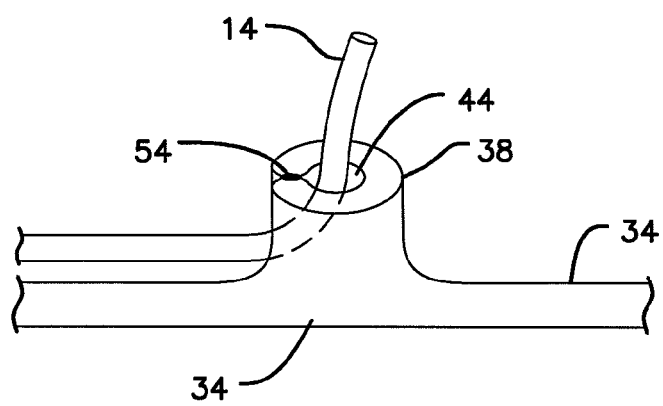
FIG. 17 is a schematic side view of an example balloon arrangement comprising an end mated arc balloon member defining a centered distal opening and a side proximal opening
Figure 18:
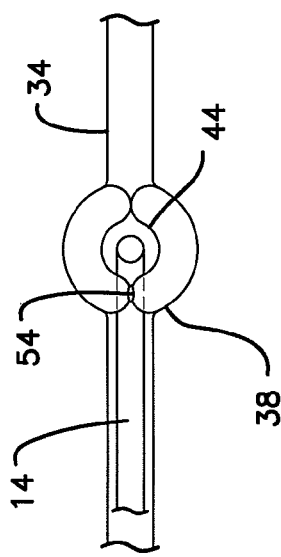
FIG. 18 is a top view of the balloon arrangement of FIG. 17.

FIGS. 9 and 10 illustrate two generally curved portions 46, 48 for the second inflatable member 38 that together define the passage 44. FIGS. 17 and 18 illustrate a single portion second inflatable member 38 where opposing ends of the member are brought together to define a donut-type shape having a passage 44 defined therein. The ends of the member 38 can be connected together using, for example, any connection means such as, for example, heat welding and adhesives.

The second inflatable member 38 shown in FIGS. 3A-14, 17 and 18 are shown integrally formed with the second branch portion 34. The second inflatable members 38 can be formed integrally with the second branch portion 34 using known balloon manufacturing techniques, such as those described in co-pending U.S. Published Application No. 2005/015108 titled CATHETER BALLOON SYSTEMS AND METH- ODS, which is incorporated herein by reference. Alternatively, the second inflatable member 38 can be formed as a separate piece and secured to an outer surface of the first inflatable member 36 in a separate step. An example separately formed inflatable member 38 is described with reference to FIGS. 15-16.

Figure 15:
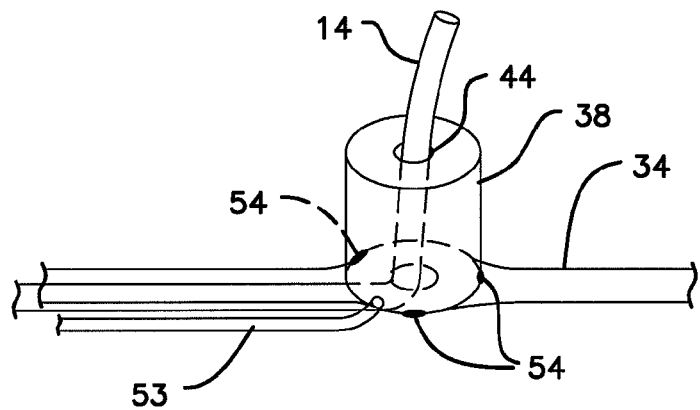
FIG. 15 is a schematic side view of an example balloon arrangement comprising a separate cylindrical shaped inflatable member defining a centered distal opening and a side proximal entrance between the cylindrical inflatable member and a main body of the side branch balloon.
Figure 16:
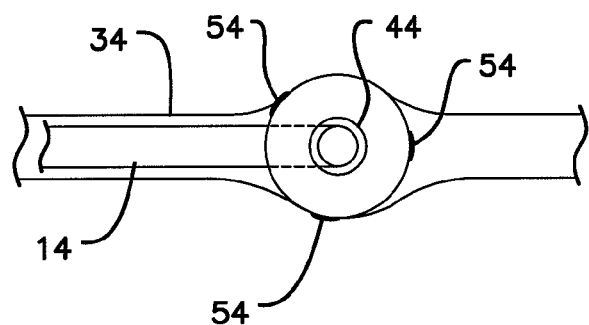
FIG. 16 is a top view of the balloon arrangement of FIG. 15.

Another type of structure for use as the second inflatable member 38 is shown in FIGS. 15 and 16. The inflatable member 38 of FIGS. 15 and 16 has a generally cylindrical shape with a donut shaped cross section. A donut shaped cross section is defined as having a generally circular outer circumference and a generally circular aperture extending along an axis of the structure. The second inflatable member 38 is formed as a separate piece that is connected to the second branch portion 34. The second inflatable member 38 shown in FIGS. 15 and 16 can be connected to the second branch portion 34 using, for example, heat welding or adhesives at connection points 54. Any number of connection points 54 can be used to connect the second inflatable member 38 to the second branch portion 34. In the illustrated example, three connection points 54 are used. Further, the second branch portion 34 can be connected to the second inflatable member 38 at different locations besides along the bottom surface as shown in FIGS. 15 and 16. For example, the second branch portion 34 can be connected along a sidewall defined between top and bottom surfaces of the second inflatable member 38.

The inflatable member 38 can be inflated through an inflation lumen 53 that extends separate from the branch portion 34. The inflation lumen 53 can be in fluid communication with a source of inflation fluid used to inflate the first inflatable member 36 of the catheter assembly 100 to provide simultaneously inflation of the members 36, 38. Alternatively, the inflation lumen 53 can be coupled to a separate source of inflation fluid for simultaneous or sequential inflation of the members 36, 38.

Extending the side catheter branch 14 through a portion of the second inflatable member 38 alters a direction in which the side catheter branch extends. Prior to advancing the side catheter branch 14 through the passage 44, the side catheter branch 14 extends generally parallel with the main catheter branch 12. When a distal end portion of the side catheter branch 14 extends through the passage 44, the distal end portion is directed radially away from the main catheter branch 12. Variables such as the configuration of the passage 44 (e.g., size, shape, and relative positions of openings into and out of the passage) and the extend of inflation of the second inflatable member 28 can alter the angle at which the distal end portion of the side catheter branch 14 is directed radially away from the main catheter branch 12.

The example bifurcation treatment catheters 100 described above with reference to FIGS. 3A-18 can be used for delivery of a stent (e.g., stent 60 shown in FIGS. 19 and 23) to the vessel bifurcation 16. An example stent used for treatment of a vessel bifurcation includes a side opening along the length of the stent between proximal and distal ends of the stent. The side opening can be surrounded by expandable structure. The expandable structure is extended into an expanded position directed radially outward from the circumferential profile of the stent upon inflation of second inflatable member 38. Typically, an axial and radial position of the second inflatable member 38 relative to the side opening of the stent is fixed prior to delivery of the stent to the vessel bifurcation.

The distal end of the side branch catheter 14 typically extends into the proximal end of the stent, out of the side opening of the stent, and into the branch vessel of the vessel bifurcation. Axial and radial alignment of the second inflatable member 38 relative to the ostium of the branch vessel 20 typically also axially and radially aligns the side opening with the ostium of the branch vessel. Using the passage 44 in the second inflatable member 38 as described with reference to FIGS. 5-18 not only helps to more accurately axially and radially align the second inflatable member 38 with the stent side opening, but also helps to both axially and radially align the stent side opening relative to the ostium of the branch vessel 20. Maintaining axial and radial alignment of the side opening relative to the ostium of the branch vessel during inflation of the first and second inflatable members 36, 38 can improve alignment of the expandable structure surrounding the side opening of the stent within the branch vessel 20 when the second inflatable member 38 is inflated.

Expansion of the inflatable member 38 when aligned radially and axially with the side opening of the stent can result in expanding the size of the side opening. An increased size of the side opening can be useful for later advancing other treatment devices through the side opening into the branch vessel. In one example, a separate stent structure is at least partially positioned within the increased sized side opening for treatment of the branch vessel 20. In other examples, other balloon expandable members are extended through the expanded side opening into the branch vessel for treatment of the branch vessel 20.

IV. The Side Branch Balloon Embodiment of FIGS. 19-23

Referring now to FIGS. 19-23, another example bifurcation treatment catheter 200 is shown and described. The catheter 200 can be used to deploy a stent 60 at a vessel bifurcation 16. The catheter 200 includes main and side catheter branches 112, 114, which are advanced over main and branch guidewires 22, 24 for treatment of the main and branch vessels 18, 20 of the vessel bifurcation 16.

The main catheter branch 112 includes a distal end 130 and an inflatable member 136. The inflatable member 136 is an elongate tubular shaped structure. Distal and proximal markers 156, 158 are positioned along the main catheter branch 112. The side catheter branch 114 includes a second inflatable member 138. The side catheter branch 114 includes distal and proximal markers 78, 80. The side catheter branch 114 also includes a guidewire lumen 72 and an inflation lumen 74 (see FIGS. 20 and 21). The side catheter branch 114 can also include a proximal guidewire opening 76 proximal of the first inflatable member 136 through which the branch guidewire 24 extends.

The side catheter branch 114 is connected at its proximal end to the main catheter branch 112. The inflation lumen 74 of the side catheter branch 114 can be in fluid communication with a source of inflation fluid that provides fluid to the first inflatable member 136. Alternatively, the inflation lumen of the side catheter branch 114 remains out of fluid communication with the source of inflation fluid that provides fluid to the first inflatable member 136. Connection of the side catheter branch 114 to 10 the main catheter branch 112 helps to maintain relative positioning of the second inflatable member 138 to the first inflatable member 136. A distal end of the side catheter branch 114 can be releaseably connected to the main catheter branch 112.

When the stent 60 is positioned over the first inflatable member 136, the stent can be secured to at least one of the branches 112, 114, for example, at a proximal end of the stent 60. Alternatively, the stent 60 can also be releaseably secured to both of the catheter branches 112, 114. One example method of removably connecting the stent to the main and side catheter branches 112, 114 is to crimp the stent 60 to an exterior of the first inflatable member 136. Expansion of the stent 60 by inflating the inflatable members 136, 138 releases the stent from the catheter branches 112, 114 so 20 that the catheter 200 can be retracted from the vessel bifurcation 16.

In an alternative arrangement, the proximal end of the side catheter branch 114 remains detached from the main catheter branch 112. In this arrangement, the side and main catheter branches 114, 112 are separately adjustable relative to each other. Typically, the stent 60 is connected to both of the side and main catheter 25 branches 114, 112 in order to fix the position of second inflatable member 138 relative to the lateral branch opening 62 of the stent 60. However, alternative arrangements provide for independent axial and radial movement of the side catheter branch 114 relative to the main catheter branch 112 and the stent 60.

Figure 19:
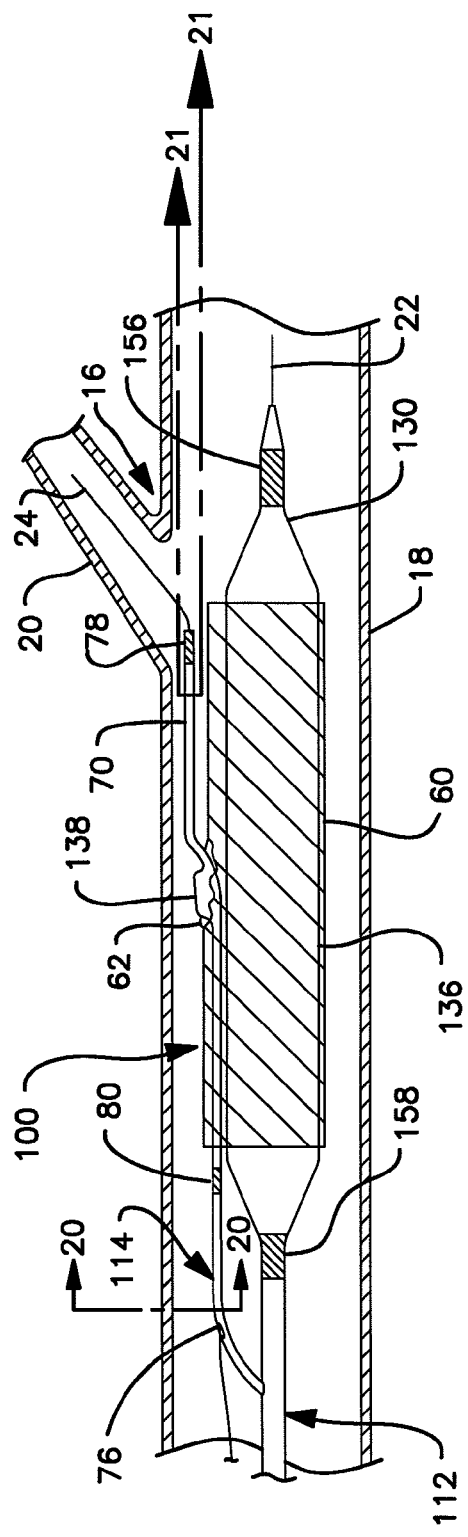
FIG. 19 is a schematic side view showing another example catheter assembly and stent, wherein the side branch lumen extends through a balloon arrangement of the catheter assembly and the catheter assembly is positioned adjacent to a vessel bifurcation.

In operation, the guidewires 22, 24 are positioned within the main and branch vessels 18, 20 of the vessel bifurcation 16 as shown in FIG. 19. The proximal ends of the main and branch guidewires 22, 24 are inserted into the distal ends 130, 70 of the main and side catheter branches 112, 114, respectively. The main and side catheter branches 112, 114 are advanced over the guidewires 22, 24 until the side catheter branch 114 extends into the branch vessel 20 as shown in FIG. 22. Typically, the system 200 is advanced distally until tension is felt by the physician due to engagement of the side catheter branch distal end 70 with the carina 17 of the vessel bifurcation. When this tension is felt, the lateral branch opening 62 of the stent 60 is generally aligned both axially and radially relative to the ostium of branch vessel 20. Depending on, for example, the size and shape of the second inflatable member 138, the physician can further advance, retract, or rotate the side catheter branch 114 to further align the second inflatable member 138 relative to the ostium of branch vessel 14. The first and second inflatable members 136, 138 are then inflated either simultaneously or sequentially. Inflation of the inflatable members 136, 138 expands the stent 60 and enlarges the lateral branch opening 62 (see FIG. 23). If expandable structure surrounds the lateral branch opening 62, inflation of the second inflatable member 130 extends the expandable structure radially outward from the main body of the stent 60 and into the branch vessel 20.

The markers 78, 80 of the side catheter branch 114 and the markers 156, 158 of the main catheter branch 112 can be used to help confirm axial and radial alignment of the stent lateral branch opening 62 relative to the ostium in the branch vessel 20. Various markers, marker materials, and marker arrangements are described in U.S. Pat. No. 6,692,483 to Vardi, and co-pending U.S. Provisional Patent Application Ser. No. 60/776,149, filed on Feb. 22, 2006, and entitled MARKER ARRANGEMENT FOR BIFURCATION CATHETER, which patent matters are incorporated herein by reference.

One example arrangement for the markers 78, 80 and 156, 158 is shown with reference to FIG. 19. The markers 78, 80 are positioned axially between the markers 156, 158. More specifically, a distal end of the marker 78 is positioned proximally of a proximal end of marker 156, and a proximal end of the marker 80 is positioned distally of a distal end of marker 158. In alternative arrangements, the markers 156, 158 are positioned axially between the markers 78, 80. In still further arrangements, one of the markers 78, 80 is positioned between the markers 156, 158, and the other of the markers 78, 80 is positioned distally or proximally of both of the markers 156, 158. The markers 78, 80 may have a different size (e.g. length) as compared to the markers 156, 158 in order to better distinguish between markers used on the catheter branches 112, 114. Additional markers can be included to illustrate, for example, the position of the second inflatable member 138, or a point along the length of the first inflatable member 136 aligned axially with the stent lateral branch opening 62. Relative positioning of the four markers 78, 80, 156, 158 can provide information about relative twists between the main and side catheter branches 112, 114. Information about relative twists can be used by a physician to improve axial and radial alignment of the stent lateral branch opening 62 and second inflatable member 138 relative to the ostium of branch vessel 20.

The side catheter branch 114 includes the second inflatable member 138 near the distal end 70 of the side catheter branch 114. The second inflatable member 138 is configured such that when expanded the member 138 extends in a direction radially outward from the outer surface of the first inflatable member 136 (e.g., in a direction perpendicular to a longitudinal axis of the first inflatable member 136). Alternatively, the second inflatable member 138 can be arranged to extend in a direction when inflated that is at an angle between radially outward and a direction parallel with a longitudinal axis of the first inflatable member 136.

Figure 21:
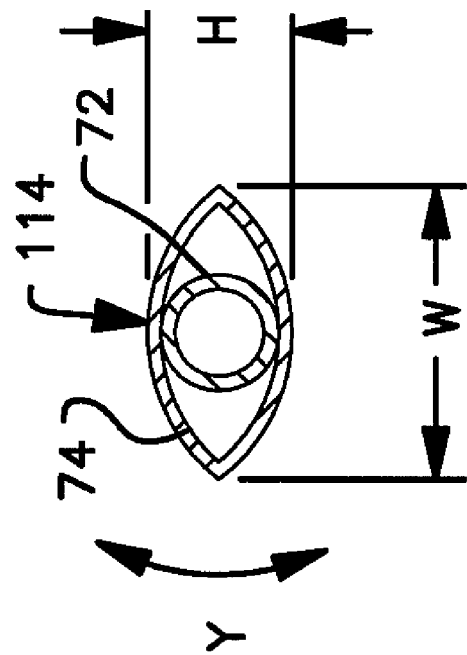
FIG. 21 is a schematic cross-sectional view of a portion of the catheter assembly shown in FIG. 19 taken along cross-sectional indicators 21-21.
Figure 20:
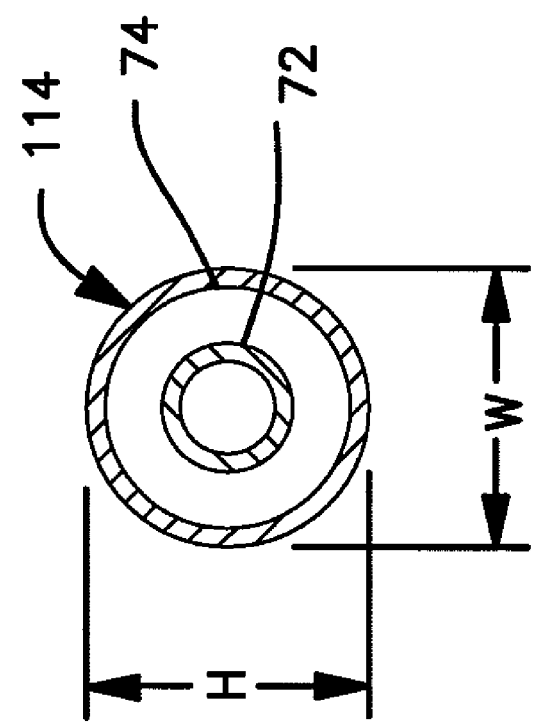
FIG. 20 is a schematic cross-sectional of a portion of the catheter assembly shown in FIG. 19 taken along cross-sectional indicators 20-20.

The second inflatable member 138 can be positioned on the side catheter branch 114. Typically, the second inflatable member 138 is integrally formed with the side catheter branch 114. Alternatively, the second inflatable member 138 is formed as a separate piece that is mounted to the side catheter branch 114 in a separate step. An inflation lumen separate from the side catheter branch 114 can be used to inflate and deflate the second inflatable member 138. In an alternative arrangement, the side catheter branch 114 extends through an interior of the second inflatable member 138. Typically, the side catheter branch 114 includes at least a guidewire lumen 72 through which the branch guidewire 24 can pass through. FIGS. 20 and 21 illustrate how the guidewire lumen 72 can extend coaxially within an inflation lumen 74 that is in fluid communication with the second inflatable member 138.

The second inflatable member 138 is positioned on a feature of catheter 200 (e.g., the side catheter branch 114) that extends into the branch vessel 20 and is used to axially and radially align the stent lateral branch opening 62 relative to the ostium of the branch vessel 20. The feature of the catheter 200 (e.g., the side catheter branch 114) on which the second inflatable member 138 is positioned is separate from a main catheter branch 112 of the catheter 200, which maintains a position within the main vessel of the vessel bifurcation 16.

Positioning the second inflatable member 138 along the length of the side catheter branch 114 provides certain advantages compared to, for example, positioning the second inflatable member 138 on the main catheter branch 112 (e.g., see catheter 100 described above). One such advantage relates to the opportunity to eliminate the second branch portion of the main catheter branch because the second branch portion is not required to carry the second inflatable member 138. Elimination of the second branch portion reduces the amount of material required for the catheter 200. The elimination of the second branch portion also reduces the cross-sectional profile of the catheter 200 and a related cross-sectional profile of the stent 60 positioned over the catheter 200. In particular, the distal portion of the catheter 200 with stent 60 near the distal end 130 can be reduced with the elimination of the second branch portion of the main catheter branch.

Another advantage of positioning the second inflatable member 138 on the side catheter branch 114 relates to improved alignment of the second inflatable member 138 relative to the ostium of the branch vessel 20. The second inflatable member 138 can be automatically at least partially aligned both axially and radially relative to the ostium of the branch vessel 20 when positioning the second inflatable member 138 on the side catheter branch 114 as a result of merely advancing the side catheter branch 114 over the guidewire 24 into the branch vessel 20.

A further advantage related to alignment is that having the side catheter branch 114 extend through the second inflatable member 138 allows the side catheter branch 114 to exit from within the stent 60 through the lateral branch opening 62 at a location further distally relative to the lateral branch opening 62. This further distal positioning can reduce the need to retract the catheter 200 proximally during the procedure in order to axially align the lateral branch opening 62 of the stent with the ostium of branch vessel 20 after engagement of the distal end 70 with the carina 17.

Eliminating the second branch portion of the main catheter branch also eliminates a manufacturing step of attaching the second branch portion to the first branch portion of the main catheter branch.

Reducing the profile of the catheter 200 and stent 60 can provide more similar sized profiles of the main and side catheter branches 112, 114. Making the main and side catheter branches 112, 114 of similar profile can improve deliverability of the catheter 200 to the vessel bifurcation and lessen the chances of damage to the catheter 200 while passing through any relative twists of the guidewires 22, 24.

Another potential advantage of positioning the second inflatable member 138 on the side catheter branch 114 relates to re-inflation of the catheter 200. Typically, rotation of the catheter branches 112, 114 can arise when inflating the inflatable members 136, 138, and then again when the re-inflating the inflatable members 136, 138 after at least partially deflating the members 136, 138. Rotation of the branches 112, 114 after axial and radial alignment with the ostium of branch vessel 20 has been established can result in the stent lateral branch opening 62 rotating out of alignment with the ostium of the branch vessel 20. Positioning the second inflatable member 138 along the side catheter branch 114 helps maintain both axial and radial positioning of the stent lateral branch opening 162 during inflation, deflation, and re-inflation of the first and second inflatable members 136, 138 during expansion of the stent 60.

FIG. 21 illustrates the distal end 70 of the side catheter branch 114 having a generally clamshell shaped cross section for the inflation lumen 74. The clamshell shape of the inflation lumen 74 cross section includes two arch shaped halves with the concave side of each half facing each other. The cross section of the inflation lumen 74 shown in FIG. 21 has a greater width W than a height H. Other alternative configurations are possible that provide an inflation lumen with a height to width ratio less than 1 as compared to the height to width ratio of 1 for the circular cross-section shown in FIG. 20. Typically, the inflation lumen 74 is arranged with the width feature aligned transverse to an axis of the stent opening and the height feature is aligned parallel with the axis of the stent opening.

Reducing the profile of the side catheter branch 114 can provide advantages over full sized side catheter branch profiles. Further, shaping the side catheter branch 114, for example using an inflation lumen height to width ratio less than 1 for portions of the inflation lumen, can provide advantages over other cross sectional shapes. In one arrangement, the inflation lumen has a reduced profile along that portion of the side catheter branch 114 between the second inflatable member 138 and the distal tip of the side catheter branch 114. The reduced profile can provide improved maneuverability of the side catheter branch 114 and the catheter 200 generally through the vessel to the vessel bifurcation 16. Providing a height to width ratio less than 1 can result in automatic orienting of the second inflatable member 138 facing radially outward towards the stent side opening. Rotation in the directions X shown in FIG. 21 is inhibited because the rest state of the side catheter branch 114 is the position shown in FIG. 21 with the second inflatable member 138 facing radially outward toward the ostium of branch vessel 20. A height to width ratio less than 1 can also provide improved bending of the side catheter branch 114 from the main vessel 18 into the branch vessel 20.

The inflation lumen 74 can be formed with the generally flattened profile shown in FIG. 21 during manufacturing of the side catheter branch 114. Manufacturing methods such as extrusion and molding can be used to generate the desired cross-sectional shape for the side catheter branch 114. Alternatively, additional structures can be secured to an outer surface of the side catheter branch 114, wherein the structures have a predefined shape that alters the cross section of the side catheter branch 114. In one example, the additional structure is a clamp that extends at least partially around a circumference of the side catheter branch and has a generally oval shape. In another example, the marker 78 is crimped onto an outer surface of the side catheter branch 114 thereby altering the outer profile of the branch 114. A plurality of additional structures can be positioned along a length of the side catheter branch 114 to provide various cross sectional shapes.

In other example arrangements, the side catheter branch 114 can include structure imbedded within the branch 114 that biases the inflation lumen 74 into the desired cross sectional shape. In further alternatives, the inflation lumen 74 ends at the second inflatable member 138 and only the guidewire lumen 72 extends from the second inflatable member 138 to the distal tip of the side catheter branch 114. The guidewire lumen 72 can also be shaped into a desired flattened profile so long as the guidewire lumen 72 still maintains a sufficient interior size for passing over the guidewire 24.

V. The Catheter Assembly of FIGS. 24-28

FIGS. 24-26 illustrate another bifurcation treatment catheter 200 associated with a stent 60. The catheter 200 includes main and side catheter branches 212, 214 configured to advance over main and branch guidewires 22, 24, respectively, for treatment of a vessel bifurcation, such as the vessel bifurcation 16 shown in FIG. 19. The main catheter branch 212 includes a distal end 230, first and second branch portions 232, 234, and first and second inflatable members 236, 238 associated with the branch portions 232, 234, respectively. The main catheter branch 212 also includes distal and proximal markers 256, 258 and a main guidewire lumen 259 (see FIG. 25). The markers 256, 258 can be constructed and arranged as disclosed in U.S. Pat. No. 6,692,483 and U.S. Provisional Patent Application No. 60/776,149 referenced above.

The side catheter branch 214 includes a distal end 270, a guidewire lumen 272, distal and proximal markers 278, 280, a dual lumen connector 284, and a balloon branch lumen 286 within the connector 284 (see FIG. 25). The lumens 272, 286 are arranged in a stacked orientation with the lumen 272 positioned radially further from the first branch portion 232 of the main catheter branch 212. The dual lumen connector 284 is illustrated in FIGS. 24-26 as being integrally formed with the side catheter branch 214. Alternatively, the dual lumen connector 284 can be formed as a separate piece that is connected to the side catheter branch 214 or to the second branch portion 234 of the main catheter branch 212.

The dual lumen connector 284 connects the side catheter branch 214 directly to the second branch portion 234. Connection of the side catheter branch 214 to the second branch portion 234 aligns the side catheter branch 214 radially with the second inflatable member 238. The second inflatable member 238 can be used to treat a branch vessel of the vessel bifurcation. Treatment of the branch vessel occurs when the second inflatable member 238 expands radially outward toward the ostium of the branch vessel. When the second inflatable member 238 is positioned within a stent 60 as shown in FIG. 26 and in alignment with a lateral branch opening 62 of the stent 60, inflation of the second inflatable member 238 can result in expansion of the lateral branch opening 62 and radially outward extension of expandable structure of the stent 60 that surrounds the lateral branch opening 62. Examples of expandable structure of the stent 60 that surrounds the lateral branch opening 62 and a variety of side opening configurations are disclosed in U.S. Pat. Nos. 6,210,429 and 6,325,826, co-pending U.S. Published Application Nos. 2004/013873 and 2005/0015108, and co-pending U.S. patent application Ser. No. 10/644,550. Radial and axial alignment of the second inflatable member 238 relative to the lateral branch opening 62 is important for proper treatment of the vessel bifurcation 16 using the stent 60 and catheter 200.

Connecting the side catheter branch 214 to a feature of catheter 200 that carries the second inflatable member 238 can improve radial and axial alignment of the stent side opening relative to an ostium of a branch vessel. During operation, the side catheter branch 214 extends through the lateral branch opening 62 and into the branch vessel of the vessel bifurcation, thus at least partially radially and axially aligning the lateral branch opening 62 with the ostium of the branch vessel 14. When the side catheter branch 214 is connected to the second branch portion 234 using the dual lumen connector 284, the second inflatable member 238 also generally aligns both radially and axially relative to the ostium of the branch vessel 14.

The dual lumen connector 284 can be positioned along the second branch portion 234 at any location between the second inflatable member 238 and a proximal end of the second branch portion 234 where the second branch portion 234 connects with the first branch portion 232. The dual lumen connector 284 can be positioned within the stent 60 or outside of the stent 60.

In an alternative arrangement, the second inflatable member 238 is integrated with the first branch portion 232, and the second branch portion 234 is eliminated. In this arrangement, the dual lumen catheter 284 can be configured for connection to the first branch portion 232. In one example, the dual lumen connector 284 includes a balloon branch lumen 286 that is sized for a portion of the first branch portion 232 to pass there through. In other arrangements, the dual lumen connector 284 is connected to a portion of the first inflatable member 236. In still further arrangements, the dual lumen connector 284 is replaced with an alternative connector that connects an exterior surface of a portion of the main catheter branch 212 to the side catheter branch 214 rather than having a portion of the main catheter branch 212 extend through the connector. Alternatively, the dual lumen connector 284 can be integrally formed with the second branch portion 234 and have a side catheter branch lumen sized to receive the side catheter branch 214.

As discussed above, a primary aspect of the example catheter 200 shown in FIGS. 24-26 is providing a predictable radial position of the side catheter branch 214 relative to the main catheter branch 212 and particularly with the second inflatable member 238. Providing such a fixed relative radial positioning of the side catheter branch 214 with the second inflatable member 238 can provide radial alignment of the second inflatable member 238 with an ostium of a branch vessel.

Figure 27:
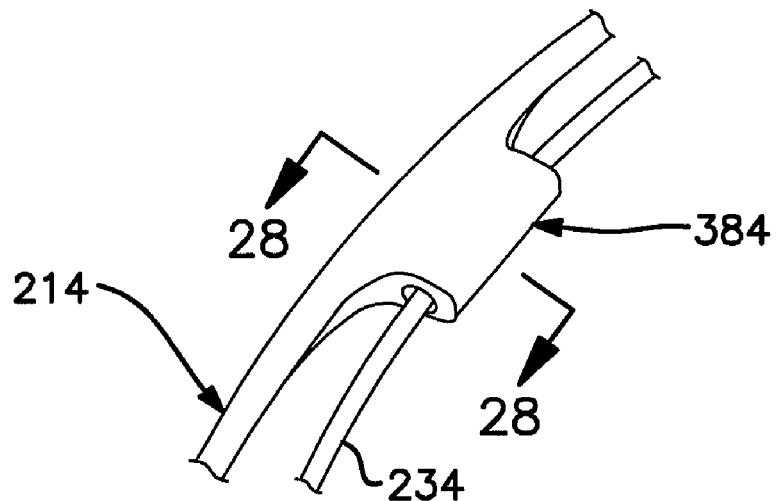
FIG. 27 is a perspective view of another dual lumen connector having lumens in a side-by-side arrangement.
Figure 28:
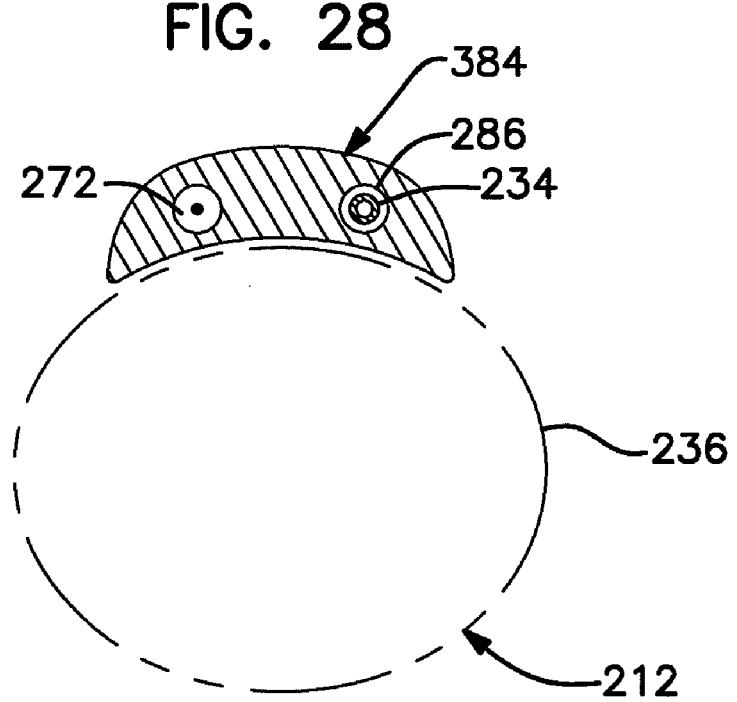
FIG. 28 is a cross-sectional view of the dual lumen connector shown in FIG. 27.

FIGS. 27 and 28 illustrate another example dual lumen connector 384. The connector 384 defines a guidewire lumen 272 that extends continuously from a guidewire lumen defined by the side catheter branch 214. The connector 384 further defines lumen 286 sized to receive the second branch portion 234. The lumens 272, 286 are arranged side-by-side generally the same radial distance from the main catheter branch 212. Arranging the lumens 272, 286 side-by-side provides a side-by-side orientation of the side catheter branch 214 and second branch portion 234. Positioning the side catheter branch 214 and second branch portion 234 side-by-side can result in a reduced profile for the catheter and potentially more predictable orientation of the side catheter branch 214 relative to the second inflatable member 238.

V. Summary and Conclusion

One aspect of the present disclosure relates to a catheter assembly that includes a catheter shaft having a distal end, a side catheter branch, and a main catheter branch arrangement extending from the distal end of the catheter shaft. The main catheter branch arrangement includes a main balloon and a branch balloon. The branch balloon includes a pre-formed side catheter branch receiver therein. The branch balloon extends radially outward relative to the main balloon when in an inflated state. The side catheter branch extends through the pre-formed side catheter branch receiver to align the side catheter branch relative to the branch balloon.

Another aspect of the present disclosure relates to a catheter assembly that includes a catheter shaft having a distal end portion, a main catheter branch, a side catheter branch, a main balloon, and a branch balloon. The main catheter branch extends from the distal end portion of the catheter shaft and includes first and second main branch portions. The main balloon is positioned on the first main branch portion. The branch balloon is position on the second main branch portion. The branch balloon includes a pre-formed side catheter branch receiver. The side catheter branch extends through the pre-formed side catheter branch to align the side catheter branch relative to the branch balloon.

A further aspect of the present disclosure relates to a method of treating a vessel bifurcation with a catheter assembly. The vessel bifurcation includes a main vessel and a branch vessel. The catheter assembly includes a catheter shaft having a distal end, a main catheter branch extending from the distal end of the catheter shaft, a side catheter branch, and main and branch balloon portions positioned on the main catheter branch. The branch balloon extends radially relative to main catheter branch when inflated, and includes a pre-formed side catheter branch receiver. The method includes positioning the main catheter branch within the main vessel, and extending the side catheter branch through the preformed side catheter branch receiver to locate the side catheter branch relative to the branch balloon.

A still further aspect of the present disclosure relates to a catheter assembly that includes a catheter shaft having a distal end, a side catheter branch, and a main catheter branch arrangement extending from the distal end of the catheter shaft. The main catheter branch arrangement includes first and second main branch portions, a main balloon positioned on the first main branch portion, and a branch balloon positioned on the second main branch portion. A proximal end of the second main branch portion is secured to the first main branch portion proximally of a proximal end of the main balloon. The assembly further includes a connector secured to the side catheter branch and secured to the second main branch portion at a location between the proximal end of the second main branch portion and the branch balloon. The connector aligns the side catheter branch relative to the branch balloon.

It is noted that not all of the features characterized herein need to be incorporated within a given arrangement, for the arrangement to include improvements according to the present disclosure.

We claim:

1. A catheter assembly, comprising:
   (a) a catheter shaft having a distal end;
   (b) a main catheter branch arrangement extending from the distal end of the catheter shaft, the main catheter branch arrangement defined by one or more side walls, the main catheter branch arrangement including a main balloon and a branch balloon, the branch balloon including a pre-formed side catheter branch receiver therein, the branch balloon extending radially outward relative to the main balloon when in an inflated state; and
   (c) a side catheter branch extending in a side-by-side arrangement with the main catheter branch arrangement, wherein the side catheter branch is defined by a side catheter side wall that is separate and distinct from each of the one or more side walls of the main catheter branch arrangement, wherein a portion of the side catheter branch is configured to extend through the pre-formed side catheter branch receiver to align the side catheter branch relative to the branch balloon
   (d) wherein the main catheter branch arrangement includes first and second main branch portions, the main balloon positioned on the first main branch portion and the branch balloon positioned on the second main branch portion, a proximal end of the second branch portion secured to the first branch portion proximal of a proximal end of the main balloon.

2. The catheter assembly of claim 1, wherein the branch balloon is positioned on the main balloon portion.

3. The catheter assembly of claim 1, wherein the pre-formed side catheter branch receiver defines an aperture centrally located on a surface of the branch balloon that faces radially away from the main balloon.

4. The catheter assembly of claim 1, wherein the branch balloon includes at least first and second inflatable portion, the at least first and second inflatable portions defining a portion of the pre-formed side catheter branch receiver.

5. The catheter assembly of claim 1, wherein the first main branch portion defines an inflation lumen and a guidewire lumen that extend coaxially with each other.

6. The catheter assembly of claim 1, wherein the second main branch portion includes a distal end portion that extends distally of the branch balloon portion and defines an inflation lumen that extends through the distal end portion, and a cross section of the inflation lumen at the distal end portion has a height-to-width ratio less than 1.

7. The catheter assembly of claim 1, further comprising a stent having a lateral branch opening positioned at a location between distal and proximal open ends of the stent, a distal end portion of the side catheter branch extends through the lateral branch opening, and the expandable member is aligned radially and axially relative to the lateral branch opening.

8. The catheter assembly of claim 1, wherein a proximal end of the side catheter branch is coupled to the catheter shaft proximal of the distal end.

9. A catheter assembly, comprising:
   (a) a catheter shaft having a distal end portion;
   (b) a main catheter branch extending from the distal end portion of the catheter shaft, the main catheter branch including first and second main branch portions;
   (c) a side catheter branch extending in a side-by-side arrangement with the main catheter branch;
   (d) a main balloon positioned on the first main branch portion; and
   (e) a branch balloon including a proximal waist and a distal waist positioned on the second main branch portion, the branch balloon including a body portion defined by a sidewall extending between the proximal waist and the distal waist, the branch balloon including a pre-formed side catheter branch receiver defined by a passage extending between a first opening in the sidewall of the body portion and a second opening in the sidewall of the body portion, the side catheter branch extending through the pre-formed side catheter branch receiver to align the side catheter branch relative to the branch balloon.

10. The catheter assembly of claim 9, wherein the pre-formed side catheter branch receiver includes a channel portion sized to receive the side catheter branch, the channel portion defined prior to the side catheter branch extending through the pre-formed side catheter branch receiver.

11. The catheter assembly of claim 9, wherein the branch balloon includes at least two inflatable members which when inflated define at least a portion of the pre-formed side catheter branch receiver.

12. The catheter assembly of claim 9, wherein the pre-formed side catheter branch receiver is at least partially defined within the second main branch portion.

13. The catheter assembly of claim 9, wherein the second main branch portion includes a distal end portion that extends distally of the branch balloon, the distal end portion of the second main branch portion having a taper.

14. The catheter assembly of claim 9, wherein the branch balloon is configured as a separate piece that is secured to the second main branch portion.

15. The catheter assembly of claim 9, wherein the second main branch portion includes a distal end portion that extends distally of the branch balloon, and a cross section of the distal end portion has a height to width ratio less than 1.

16. The catheter assembly of claim 9, further comprising a stent having a lateral branch opening, the lateral branch opening positioned at a location between distal and proximal open ends of the stent, a distal end portion of the side catheter branch extends through the lateral branch opening.

17. The catheter assembly of claim 9, wherein the branch balloon is formed from a portion of the second main branch portion.

* * * * *